United States Patent
Uemura et al.

(10) Patent No.: US 7,112,441 B2
(45) Date of Patent: Sep. 26, 2006

(54) 3-DIMENSIONAL KLINOSTAT FOR CULTURE OF CELLS

(75) Inventors: Masaru Uemura, Hyogo-ken (JP); Jun-Ichiro Gyotoku, Hyogo-ken (JP); Makoto Asashima, 3-40-9 Minami-Otsuka, Toshima-ku, Tokyo (JP)

(73) Assignees: Mitsubishi Heavy Industries, Ltd., Tokyo (JP); Makoto Asashima, Tokyo (JP)

( * ) Notice: Subject to any disclaimer, the term of this patent is extended or adjusted under 35 U.S.C. 154(b) by 420 days.

(21) Appl. No.: 10/233,506

(22) Filed: Sep. 4, 2002

(65) Prior Publication Data

US 2003/0064513 A1 Apr. 3, 2003

(30) Foreign Application Priority Data

Sep. 4, 2001 (JP) ............................. 2001/267747

(51) Int. Cl.
*C12N 5/02* (2006.01)
(52) U.S. Cl. ...................... 435/394; 435/383; 435/325
(58) Field of Classification Search ................ 435/325, 435/375, 377, 382, 383, 394
See application file for complete search history.

(56) References Cited

U.S. PATENT DOCUMENTS 4,874,358 A 10/1989 Brimhall et al.
4,988,623 A * 1/1991 Schwarz et al. ......... 435/297.3
5,989,913 A * 11/1999 Anderson et al. ........... 435/394

FOREIGN PATENT DOCUMENTS

| JP | 64-56400 | 3/1989 |
|---|---|---|
| JP | 6-321700 | 11/1994 |
| JP | 7-89798 | 10/1995 |
| JP | 2000-79900 | 3/2000 |

OTHER PUBLICATIONS

McPherson, "Virus and Protein Crystal Growth on Earh and in Microgravity" J of Physics D: Applied Physics 1992, vol. 26, No. 8B, pp. B104-B112.*
Hoson et al, "Evaluation of the three-dimensional clinostat as a simulator of weightlessness" Planta, 1997, vol. 203, pp. S187-S197.*
Unsworth et al, "Growing Tissues in Microgravity" Nature Medicine, 1998, vol. 4, No. 8, pp. 901-907.*
Huijser, "Desktop RPM: New Small Size Microgravity Simulator for the Bioscience Laboratory" DESC web site, http://www.desc.med.vu.nl accessed Jun. 14, 2005.*
Keirstead, "Stem Cell Transplantation Into the Central Nervous System and the Control of Differentiation" J of Neuroscience Research, 2001, vol. 63, pp. 233-236.*

* cited by examiner

*Primary Examiner*—Leon B. Lankford, Jr.
*Assistant Examiner*—Allison M. Ford
(74) *Attorney, Agent, or Firm*—Oblon, Spivak, McClelland, Maier & Neustadt, P.C.

(57) ABSTRACT

In order to grow an object to be cultivated or grown, a growth object is encapsulated in a vessel, and the growth object is grown without substantial influence of gravity.

4 Claims, 9 Drawing Sheets

3-DIMENSIONAL KLINOSTAT FOR CULTURE OF CELLS

BACKGROUND OF THE INVENTION

1. Field of the Invention

The present invention relates to a technique using a klinostat, and more particularly, to a method of cultivating a cell lump to form an artificial organ and a method of forming material, using a klinostat.

2. Description of the Related Art

A medical technique is important to recover functions of a damaged tissue or organ using artificially cultivated tissue and organ, i.e., an artificial organ in future regeneration medicine. In order that the medical technique is realized, cell cultivation technique for cultivating a tissue or organ with a 3-dimensional structure from a cell or cell lump is indispensably necessary.

As such a cell cultivation technique, a technique is known in which a cell lump is encapsulated in a cultivation vessel filled with culture fluid, and is held in a floating state by rotating the cultivation vessel around one axis, applying vibration to the cultivation vessel, introducing air bubbles into the cultivation vessel or generating a watercourse with an impeller such that the cell lump is grown in the flowing state. In this conventional technique, however, the cell lump disperses and the cell lump suffers damage through the contact with the cultivation vessel wall. Therefore, the cultivation of a 3-dimensional tissue is supposed to be obstructed.

Also, a technique is studied in which a cell lump is cultivated in a minute gravity environment like the universe, as another cell cultivation technique. It is considered that it would be possible to cultivate a tissue with the 3-dimensional structure, because the cell lump does not sink under the minute gravity environment. Also, the possibility of the forming of a cell aggregate of a high density is shown in the minute gravity environment. However, it lacks of the practicality to cultivate a cell lump in the universe.

Also, an animal and plant growing apparatus is known in Japanese Examined Patent application (JP-B-Heisei 7-89798). In the animal and plant growing apparatus of this reference, a vessel to store an animal and plant is rotated around two or more 2 axes so that gravity is applied to the animal and plant into many directions. The animal and plant is grown in a pseudo gravity free environment.

Also, Japanese Examined Patent application (JP-B-Heisei 7-89798) discloses to grow an animal and plant and to cultivate a cell. However, a specific method to cultivate a cell is not disclosed.

SUMMARY OF THE INVENTION

Therefore, an object of the present invention is to provide a practical technique to cultivate a tissue with a 3-dimensional structure.

Another object of the present invention is to provide a technique in which cell dispersing can be prevented when a tissue with the 3-dimensional structure is formed through cultivation of a cell.

Another object of the present invention is to provide a technique which a cell can be cultivated for a long term when a tissue with the 3-dimensional structure is formed through cultivation of the cell.

Another object of the present invention is to provide a technique which the environment of cultivation of a cell can be optimized when a tissue with the 3-dimensional structure is formed through the cultivation of the cell.

Another object of the present invention is to provide a technique for forming a large tissue with the 3-dimensional structure is formed through the cultivation of the cell.

In an aspect of the present invention, in order to grow an object to be cultivated or grown, a growth object is encapsulated in a vessel; and the growth object is grown without substantial influence of gravity.

When the growth object is a cell lump, the cell lump and fluid may be encapsulated in the vessel. Also, when the growth object is a cell lump and the cell lump is adhered to an artificial matrix, the fluid, the artificial matrix, and a supporting section for supporting the artificial matrix may be encapsulated in the vessel.

Also, the artificial matrix to which the cultivated cell lump is adhered is desirably taken out as an artificial organ, after the cultivation.

Also, differentiation of the cell lump is desirably promoted.

Also, the coefficient of viscosity of the fluid is desirably adjusted such that the cell lump does not touch the vessel.

Also, the vessel is rotated around different n axes (n is an integer more than 1) such that the influence of the gravity is eliminated.

Also, it is desirable that the cell lump is cultivated while supplying the fluid to the vessel. In this case, the fluid may be circulated or dumped.

Also, when the growth object is an organism, fluid, containing material necessary for growth of the organism, is supplied into the vessel. In this case, the vessel is desirably rotated around n axes (n is an integer more than 1).

In another aspect of the present invention, culture fluid and a cell lump are encapsulated in a cultivation vessel, and the cell lump is cultivated without influence of gravity. The cultivation cell lump is held in a floating state in the culture fluid.

Also, the cultivation cell lump may be adhered to an artificial matrix. The culture fluid, the artificial matrix to which the cell lump is adhered, and a supporting section to support the artificial matrix is encapsulated in the cultivation vessel.

Also, the cultivation vessel is desirably rotated around different n axes (n is an integer more than 1).

The method may further include adjusting a coefficient of viscosity of the culture fluid such that the cell lump does not touch the cultivation vessel while the cultivation vessel is rotated around the n axes. Also, the method may further include promoting differentiation of the cell lump.

The artificial matrix to which the cultivated cell lump is adhered is taken out as an artificial organ after the cultivation.

In another aspect of the present invention, culture fluid and a cultivation cell lump are encapsulated in a cultivation vessel, and the cultivation vessel is rotated around n axes (n is an integer more than 1). The cultivation cell lump is held in a floating state in the culture fluid.

The coefficient of viscosity of the culture fluid is desirably adjusted such that the cultivation cell lump does not touch the cultivation vessel while the cultivation vessel is rotated around the n axes.

The culture fluid, an artificial matrix to which cultivation cell lumps are adhered, and a supporting section to fixedly support the artificial matrix are encapsulated in a cultivation vessel. The cultivation vessel is rotated n axes (n is an integer more than 1). Also, differentiation of the cultivation cell lumps is promoted.

In another aspect of the present invention, culture fluid, cultivation cell lumps are encapsulated in a cultivation vessel, and the cultivation cell lumps is cultivated in a state which the cultivation vessel is rotated around n axes (n is an integer more than 1), to form an artificial organ. The cultivation cell lump is held in a floating state in the culture fluid.

The coefficient of viscosity of the culture fluid may be desirably adjusted such that the cultivation cell lumps do not touch the cultivation vessel while the cultivation vessel is rotated around the n axes.

In another aspect of the present invention, culture fluid, an artificial matrix to which cultivation cell lumps are adhered, and a supporting section to fixedly support the artificial matrix are encapsulated in a cultivation vessel. The cultivation cell lumps is cultivated in a rotation state of the cultivation vessel around n axes (n is an integer more than 1). The structure of the cultivated cultivation cell lumps and the artificial matrix is taken out as an artificial organ after the cultivation.

Also, differentiation of the cultivation cell lumps is desirably promoted.

DESCRIPTION OF THE PREFERRED EMBODIMENTS

Hereinafter, a method of cultivating a cell according to the present invention will be described with reference to the attached drawings. The present invention relates to the U.S. patent application Ser. No. (10/119,895) filed Apr. 11, 2002. The disclosure of the application is incorporated herein by reference. Also, the present invention relates to the US patent application Ser. No. 10/233,566 entitled "APPLICATION APPARATUS OF 3-DIMENSIONAL KLINOSTAT AND GROWING METHOD USING THE SAME" and claiming the priority based on Japanese patent application 2001-267539. The disclosure of the application is incorporated herein by reference.

(First Embodiment)

Figure 1:
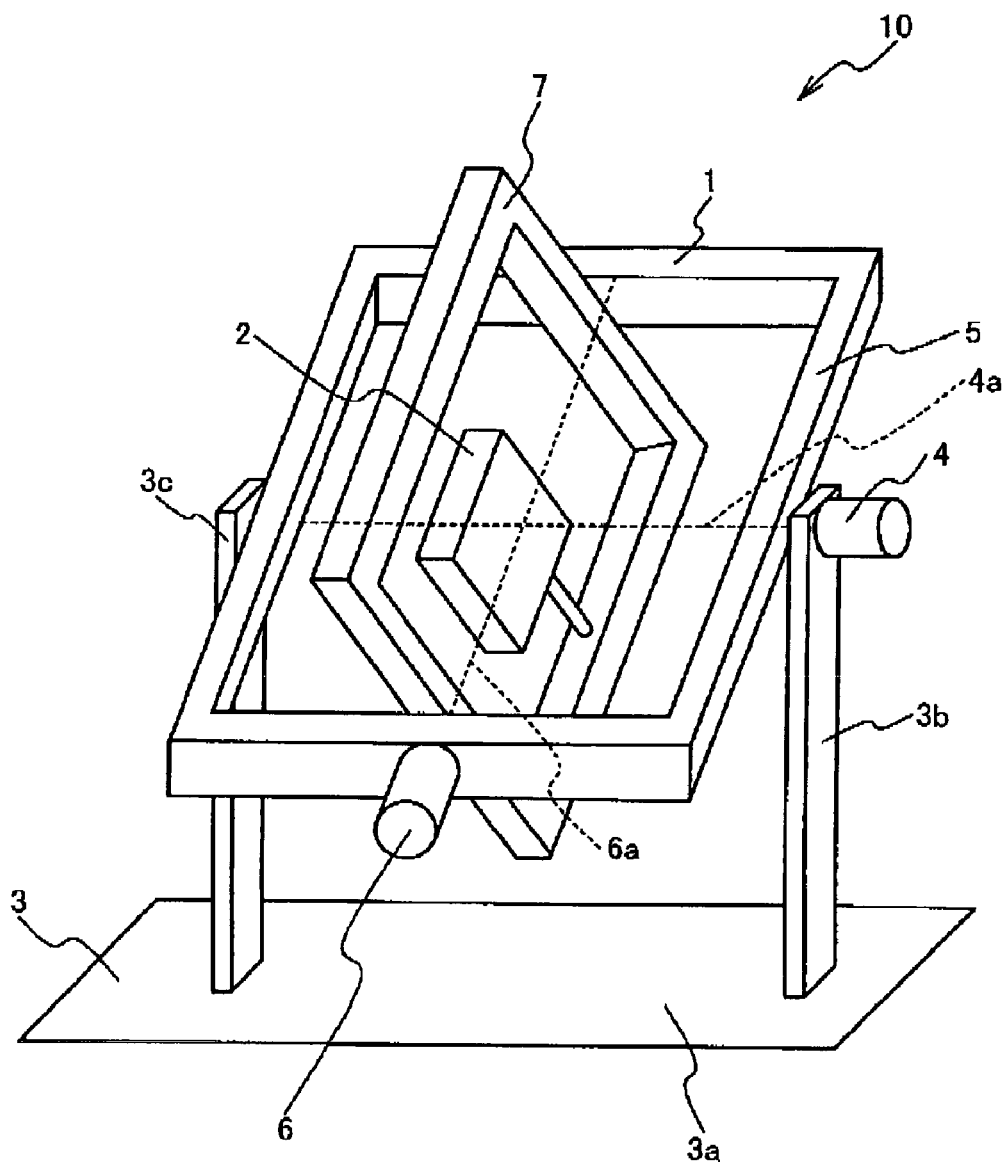
FIG. 1 is a diagram showing the cell cultivation apparatus according to a first embodiment of the present invention.

In the method of cultivating the cell according to the first embodiment of the present invention, the cell cultivation apparatus 10 shown in FIG. 1 is used. The cell cultivation apparatus 10 is comprised of a 3-dimensional klinostat 1 and a cultivation vessel 2. The 3-dimensional klinostat 1 rotates the cultivation vessel 2 around n axes (n is an integer more than 1) (n=2 in this embodiment). Culture fluid and a cultivation cell lump are encapsulated in the cultivation vessel 2. The cultivation cell is not fixed on the cultivation vessel 2 and floats in the culture fluid. A differentiation factor like activin is added to the culture fluid to promote the differentiation to the desired tissue.

The 3-dimensional klinostat 1 is composed of a main unit 3, a motor 4, an outer frame 5, a motor 6 and an inner frame 7. The main unit 3 is installed in a stationary system. The main unit 3 is composed of a base 3a and legs 3b and 3c. The legs 3b and 3c are connected with the base 3a. The motor 4 is provided for the leg 3b. The motor 4 is connected with the outer frame 5 to rotate the outer frame 5 around a rotation axis 4a. The motor 6 is provided for the outer frame 5. The motor 6 is connected with the inner frame 7 to rotate the inner frame 7 around a rotation axis 6a. The rotation axis 6a is substantially orthogonal to the rotation axis 4a. The above-mentioned cultivation vessel 2 is connected with the inner frame 7. The cultivation vessel 2 is in the neighborhood of the intersection of the rotation axis 4a and the rotation axis 6a. The cultivation vessel 2 is rotated together with the inner frame 7. When the outer frame 5 and the inner frame 7 are rotated respectively, the cultivation vessel 2 is rotated around the 2 axes. When the cultivation vessel 2 is rotated around the 2 axes, the directions of the gravity applied to the cultivation cell lump encapsulated in the cultivation vessel 2 are distributed. Thus, each cell of the cell lump can multiply to all the directions. Also, the 3-dimensional cultivation of the cultivation cell lump becomes possible. Also, the shearing force due to the liquid flow caused through the rotation of the cultivation vessel 2 around the n axes is small. The separation of the cultivation cell lump and the isolation of each cell can be prevented. Therefore, by cultivating the cell lump in the cultivation vessel 2 in the rotation state around the 2 axes, the cultivating of the tissue with the 3-dimensional structure is realized.

At this time, it is desirable that a differentiation factor like activin is added to the culture fluid when a desired tissue should be appropriately cultivated. The addition of the differentiation factor to the culture fluid makes it possible to promote the differentiation of the cultivation cell and to cultivate a tissue appropriately.

Also, it is desirable a viscosity increasing material like methylcellulose and collagen gel is added to the culture fluid. It is desirable that the coefficient of viscosity of the culture fluid is adjusted such that the cultivation cell does not touch or contact the wall of the cultivation vessel 2 when the cultivation vessel 2 is rotated around the 2 axes. Thus, the sinking of the cultivation cell lump is prevented.

Figure 2:
FIG. 2 is the outward appearance photograph of a cell lump cultivated by the cell cultivation apparatus in the first embodiment.
Figure 3:
FIG. 3 is a cross sectional photograph of the cell lump cultivated by the cell cultivation apparatus in the first embodiment.

FIG. 2 and FIG. 3 are photographs showing the outer appearance and cross section of the cell lump cultivated by the method of cultivating a cell in the first embodiment. The cell lump is cultivated by the following method. First, the A6 cell of a normal kidney of a male living body of Xenopus is adhesively cultivated for 2 weeks under the environment of 23° C. in a cultivation flask. Subsequently, a part of the cultivation cell lump multiplied in a single layer state is peeled off from the cultivation surface of the adhesion flask and is moved to the above-mentioned cultivation vessel 2. The cultivation vessel 2 is filled with culture fluid. Subsequently, the cultivation vessel 2 is rotated by the 3-dimensional klinostat 1 and the cultivation cell lump is cultivated in the cultivation vessel 2 in the floating state. The cultivation is carried out for 2 weeks under the environment of 23° C. As shown in FIG. 2, spherical cell lump was observed. Also, the formed cell lump is sliced and the internal state of the cell lump is observed. At this time, as shown in FIG. 3, the tissue like the nephridium was observed. This experiment fact shows that the tissue with the 3-dimensional structure can be formed by cultivating the cell lump by the method of cultivating a cell in the first embodiment.

It is possible to apply the method of cultivating a cell in the first embodiment to the manufacturing of an artificial organ. In this case, a cultivation cell lump, which can be differentiated to a desired organ, is encapsulated in the cultivation vessel 2. The encapsulated cell lump is cultivated while being rotated around the 2 axes to form the artificial organ with the 3-dimensional structure.

It should be noted that in the first embodiment, the cultivation vessel 2 is rotated around the 2 axes but the cultivation vessel 2 may be rotated around three or more rotation axes. In this case, like the above case of the 2-axis rotation, the directions of the gravity applied to the cultivation cell lump through the rotation of the cultivation vessel 2 are distributed, so that each cell can multiply to all the directions. Thus, the 3-dimensional cultivation of the cultivation cell lump becomes possible. Also, the shearing force of the liquid flow caused through the rotation around the n axes in the cultivation vessel 2 becomes small, so that the separation of the cultivation cell lump and the isolation of each cell can be prevented. By cultivating the cell lump in the cultivation vessel 2 in the rotation state of the cultivation vessel 2 around two or more rotation axes, the cultivation of the tissue with the 3-dimensional structure is realized.

(Second Embodiment)

In the method of cultivating a cell according to the second embodiment of the present invention, it is possible to cultivate a cell lump in the cultivation vessel by rotating the cultivation vessel filled with the culture fluid around the 2 axes, like the first embodiment. In the second embodiment, the cultivation is carried out in a state in which fresh culture fluid is continuously supplied to the cultivation vessel rotated around the 2 axes so that it is possible to cultivate for a long term.

Figure 4:
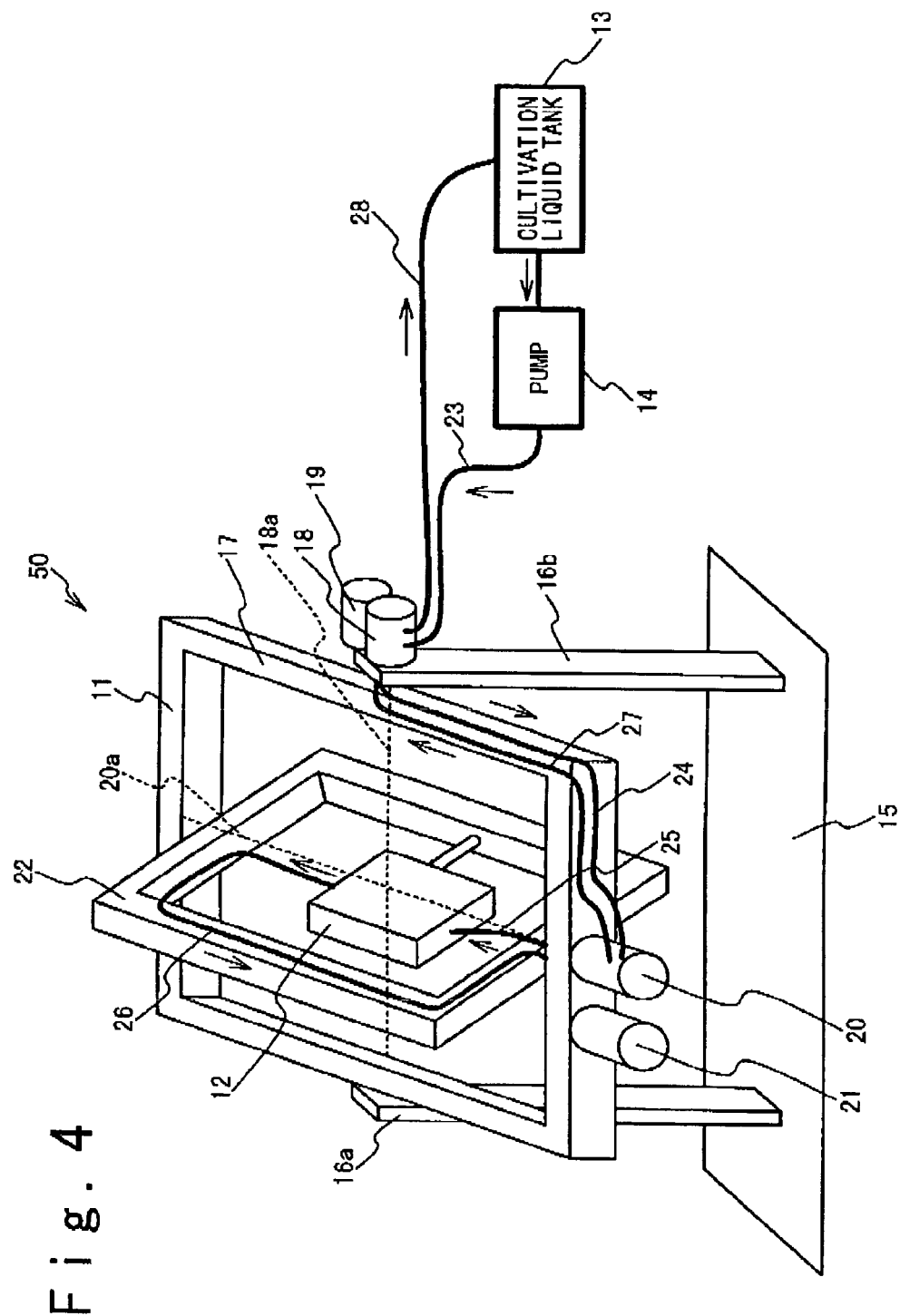
FIG. 4 is a diagram showing the cell cultivation apparatus according to a second embodiment of the present invention.

FIG. 4 shows a cell cultivation apparatus 50 used in the method of cultivating a cell according to the second embodiment of the present invention. The cell cultivation apparatus 50 is comprised of a 3-dimensional klinostat 11, a cultivation vessel 12, a culture fluid tank 13 and a pump 14. The 3-dimensional klinostat 11 rotates the cultivation vessels 12 around 2 axes. The culture fluid and a cultivated cell lump are encapsulated in the cultivation vessel 12. The cultivated cell lump is not fixed to the cultivation vessel 12 but floats in the culture fluid. A differentiation factor like activin is added to the culture fluid to promote the differentiation to a desired tissue.

The culture fluid tank 13 accumulates the culture fluid which should be supplied to the cultivation vessel 12. The pump 14 pressurizes the culture fluid accommodated in the culture fluid tank 13 and supplies to the cultivation vessel 12. The culture fluid supplied to the cultivation vessel 12 is returned to the culture fluid tank 13. Thus, the culture fluid for cultivating a cell lump is circulated.

It is desirable that the culture fluid tank 13 has a gas concentration adjusting function to control the concentration of gas contained in the culture fluid. The optimization of the concentrations of oxygen and carbon dioxide contained in the culture fluid is important in case of the cultivation of the cell lump. By adjusting the concentration of the gases contained in the culture fluid, especially, oxygen and the carbon dioxide, the cell lump can be cultivated in a more desirable environment. More specifically, the culture fluid tank 13 is formed of interchangeable material of gas, and an atmosphere around the culture fluid tank 13 is adjusted. In this way, the gases contained in the culture fluid can be controlled to the desired concentrations.

The 3-dimensional klinostat 11 has the structure different from the 3-dimensional klinostat 1 in the first embodiment, to supply the culture fluid to the cultivation vessel 12. The 3-dimensional klinostat 11 is comprised of a main unit 15. A support 16a and a support 16b are joined to the main unit 15. The support 16a supports the outer frame 17 rotatably. A rotary joint 18 and a motor 19 are joined to the support 16b. The rotary joint 18 supports the outer frame 17 rotatably. The motor 19 drives the outer frame 17 through a power transfer mechanism (not shown) such as gears and a belt, to rotate the outer frame 17 around a rotation axis 18a. A rotary joint 20 and a motor 21 are joined to the outer frame 17. The rotary joint 20 supports the inner frame 22 rotatably. The motor 21 drives the inner frame 22 through a power transfer mechanism (not shown) such as gears and a belt to rotate the inner frame 22 around a rotation axis 20a.

The above-mentioned cultivation vessel 12 is connected with the inner frame 22. The cultivation vessel 12 is in the neighborhood of an intersection of the rotation axis 18a and the rotation axis 20a. The cultivation vessel 12 is rotated together with the inner frame 22. When the outer frame 17 and the inner frame 22 are rotated respectively, the cultivation vessel 12 is rotated around 2 axes.

The supply of the culture fluid to the cultivation vessel 12 is carried out through the rotary joint 18 and the rotary joint 20 from the pump 14. The fresh culture fluid sent from the pump 14 reaches the rotary joint 18 through a supply pipe 23. The rotary joint 18 introduces the culture fluid into a supply pipe 24 which is rotated together with the outer frame 17. Also, the rotary joint 20 introduces the culture fluid into a supply pipe 25 which is rotated together with the inner frame 22. The supply pipe 25 is connected with the cultivation vessel 12, and the culture fluid is supplied to the cultivation vessel 12 from the supply pipe 25.

In the same way, the discharge of the culture fluid to the culture fluid tank 13 is carried out through the rotary joint 18 and the rotary joint 20 from the cultivation vessel 12. The cultivation vessel 12 discharges the culture fluid to a discharge pipe 26. Then, the culture fluid discharged is introduced into a discharge pipe 27, which is rotated together with the outer frame 17, through the rotary joint 20. Then, the culture fluid is introduced into a discharge pipe 28 which is put on a stationary system through the rotary joint 18. The culture fluid is returned to the culture fluid tank 13 through the discharge pipe 28.

Figure 5:
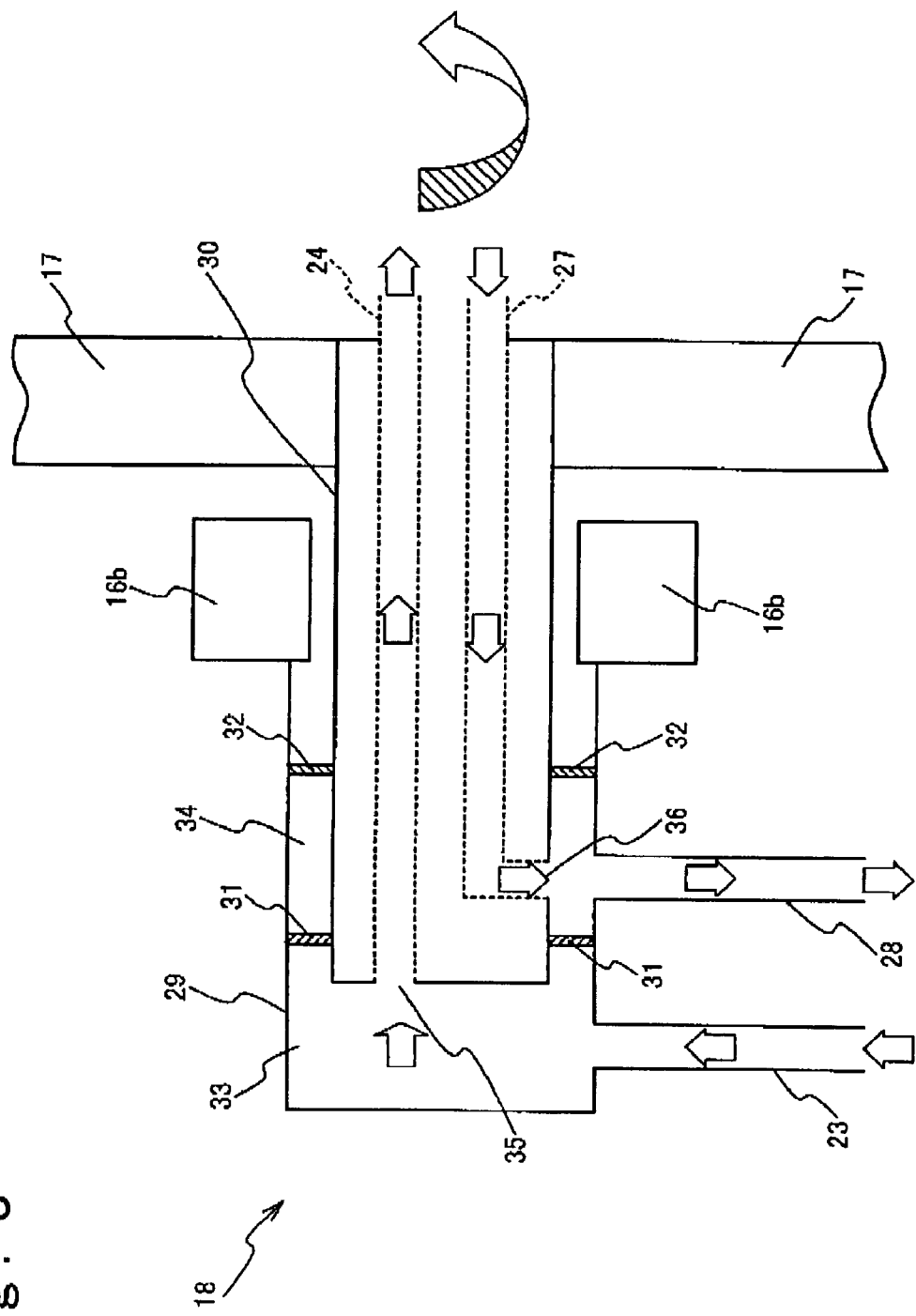
FIG. 5 is a diagram showing a rotary joint.

FIG. 5 shows the rotary joint 18 in detail. The rotary joint 18 contains a fixed section 29 and a rotation section 30. The fixed section 29 and the rotation section 30 are column bodies with different diameter. The rotation section 30 is inserted in the fixed section 29 rotatably. The fixed section 29 is fixed to the support 16b and the rotation section 30 is fixed to the outer frame 17.

In the space between the fixed section 29 and the rotation section 30, a first liquid introduction room 33 and a second liquid introduction room 34 are formed by seals 31 and 32. The first liquid introduction room 33 and the second liquid introduction room 34 are separated by the seal 31. The second liquid introduction room 34 is sealed from the external by the seal 32. The supply pipe 24 is connected with the first liquid introduction room 33 and the discharge pipe 27 is connected with the second liquid introduction room 34.

A first hole 35 opened for the first liquid introduction room 33 and a second hole 36 opened for the second liquid introduction room 34 are provided for the rotation section 30. The first hole 35 is connected with the supply pipe 24 and the second hole 36 is connected with the discharge pipe 27.

The rotary joint 18 having the above structure connects the supply pipe 23 and the supply pipe 24 and connects the discharge pipe 27 and the discharge pipe 28, regardless of the angle between the support 16b and the outer frame 17.

The rotary joint 20 has the same structure as the rotary joint 18, and connects the supply pipe 24 and the supply pipe 25 and connects the discharge pipe 26 and the discharge pipe 27, regardless of the angle between the outer frame 17 and the inner frame 22.

In this way, the culture fluid is supplied to the cultivation vessel 12 through the rotary joint 18 from outside the 3-dimensional klinostat 11 through the rotary joint 20, and the culture fluid is discharged from the cultivation vessel 12 into outside the 3-dimensional klinostat 11.

In case of supplying the culture fluid to the cultivation vessel 12 from the external, when the culture fluid flows, the disorder of the liquid flow can be caused in the cultivation vessel 12. The disorder of the liquid flow introduces the separation of the cell lump to prevent the cultivation of the 3-dimensional tissue. For this reason, the cultivation vessel 12 has the structure to restrain an influence of the disorder of the liquid flow.

Figure 6:
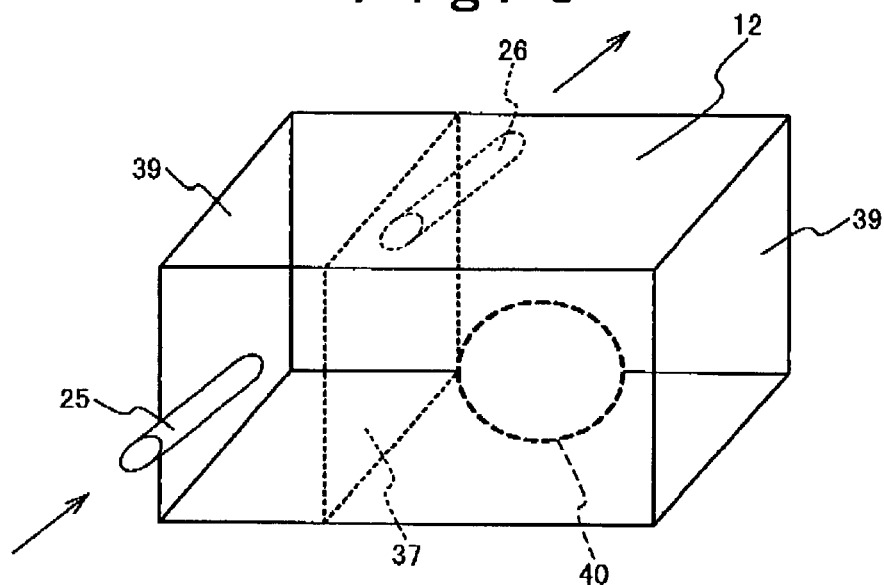
FIG. 6 is a diagram showing a cultivation vessel.

FIG. 6 shows the cultivation vessel 12. The inside of the cultivation vessel 12 is separated into a flow path room 38 and a cultivation room 39 with a separation member 37. The flow path room 38 is connected with the supply pipe 25 to supply the culture fluid and the discharge pipe 26 to discharge the culture fluid. A lot of holes (not shown) are provided for the separation member 37, so that the exchange of the culture fluid can be carried out between the flow path room 38 and the cultivation room 39 through the holes. The cell lump 40 is put in the floating state in the cultivation room 39 and the cultivation of the cell lump 40 is carried out in the cultivation room 39.

In the cultivation vessel 12 with the above structure, the culture fluid does not flow directly into the cultivation room 39 where the cultivation of the cell lump 40 is carried out. In this way, the influence of the disorder of the liquid flow by the culture fluid flowing into the cultivation vessel 12 on the cultivation of the cell lump 40 can be restrained.

The cell cultivation apparatus according to the second embodiment of the present invention, can cultivate a tissue with a 3-dimensional structure, like the first embodiment. Also, in the second embodiment, it is possible to cultivate a cell for long term.

It should be noted that the culture fluid used for the cultivation in the second embodiment is circulated. However, the culture fluid discharged from the cultivation vessel 12 may be dumped just as it is. In this case, the discharge pipe 28 used to discharge the culture fluid from the cultivation vessel 12 is not connected with the culture fluid tank 13.

(Third Embodiment)

The method of cultivating a cell according to the third embodiment of the present invention is especially applied to manufacture an artificial organ.

The method of cultivating a cell according to the third embodiment of the present invention is similar to the first and second embodiments in that the cultivation vessel filled with the culture fluid is rotated around 2 axes, and the cell is cultivated in the cultivation vessel.

The third embodiment is different from the first and second embodiments in that a cell lump is adhered to the artificial matrix which is fixed on the cultivation vessel and is cultivated in that state. In the third embodiment, gravity is applied 3-dimensionally and the 3-dimensional cultivation becomes possible in which the cell lump is adhered uniformly to the artificial matrix with the 3-dimensional structure. Also, the shearing force by the fluid stirring caused by the 2 axes rotation of the cultivation vessels is small, so that the separation and damage of the cell lump adhered and densified can be prevented.

The cultivation of the cell lump on the artificial matrix makes it possible to cultivate a large-sized artificial organ. In order to cultivate a large-sized artificial organ, it is necessary to cultivate a large-sized cell lump. However, it is difficult to keep a large-sized cell lump in the perfect floating state, and it is easy for damage to be added to the cell lump when the cell lump is large-sized. By cultivating the cell lump on the artificial matrix which is fixed on the cultivation vessel, the damage of the cell lump can be prevented and the cultivation of the large-sized cell lump becomes possible. At this time, the artificial matrix supports the cell lump fixedly and functions as a skeleton in the cultivation of the cell lump to form a part of the artificial organ.

Figure 7:
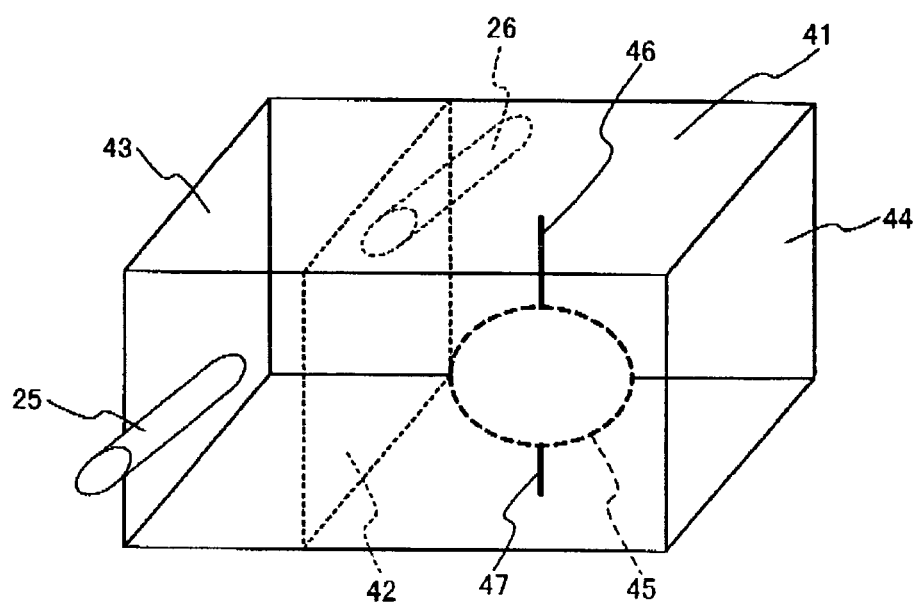
FIG. 7 is a diagram showing the cultivation vessel 42 used in the cell cultivation apparatus according to a third embodiment of the present invention.

In the third embodiment, the cultivation vessel 41 shown in FIG. 7 is used instead of the cultivation vessel 12 used in the second embodiment. The cultivation vessel 41 is separated into the flow path room 43 and the cultivation room 44 by the separation member 42. The flow path room 43 is connected with the supply pipe 25 to supply the culture fluid and the discharge pipe 26 to discharge the culture fluid. A lot of holes (not shown) are provided for the separation member 42, and the exchange of the culture fluid is carried out between the flow path room 43 and the cultivation room 44 through the holes.

The artificial matrix 45 and the artificial matrix support sections 46 and 47 are stored in the cultivation room 44. For example, the artificial matrix 45 is formed of sponge collagen. The artificial matrix 45 is used for a skeleton when a cell lump (not shown) is cultivated, and a cell lump is cultivated in the state adhered to the artificial matrix 45. The artificial matrix support sections 46 and 47 hold or support the artificial matrix 45 fixedly to the wall of the cultivation vessel 41. The cell lump cultivated by using the artificial matrix 45 and the artificial matrix support sections 46 and 47 is fixedly supported in the culture fluid.

A modification of the cell cultivation apparatus according to the third embodiment of the present invention has the same as the second embodiment and the detailed description is not carried out.

In the third embodiment, the cultivation of a tissue is carried out as follows. The cultivation cell is adhered to the artificial matrix 45. The artificial matrix 45 is fixed on the wall of the cultivation room 44 by the artificial matrix support sections 46 and 47. The inside of the cultivation vessel 41 is filled with the culture fluid. The cultivation vessel 41 is rotated around the 2 axes by the 3-dimensional klinostat 11, and the cultivation is started. During the cultivation, the pump 14 supplies the culture fluid to the cultivation vessel 41 from the culture fluid tank 13. The culture fluid discharged from the cultivation vessel 41 is returned to the culture fluid tank 13. The culture fluid flows through the cultivation room 44 3-dimensionally and the gravity is applied to the artificial matrix 45 from all directions. Thus, the cell multiplies 3-dimensionally on the surface with the artificial matrix 45.

The tissue composed of the artificial matrix 45 and the cultivation cell lump is taken out from the cultivation vessel 41 as an artificial organ. It is possible to replay or recover the function of an internal organ by transplanting the artificial organ into a body or installing it out of the body.

Figure 8:
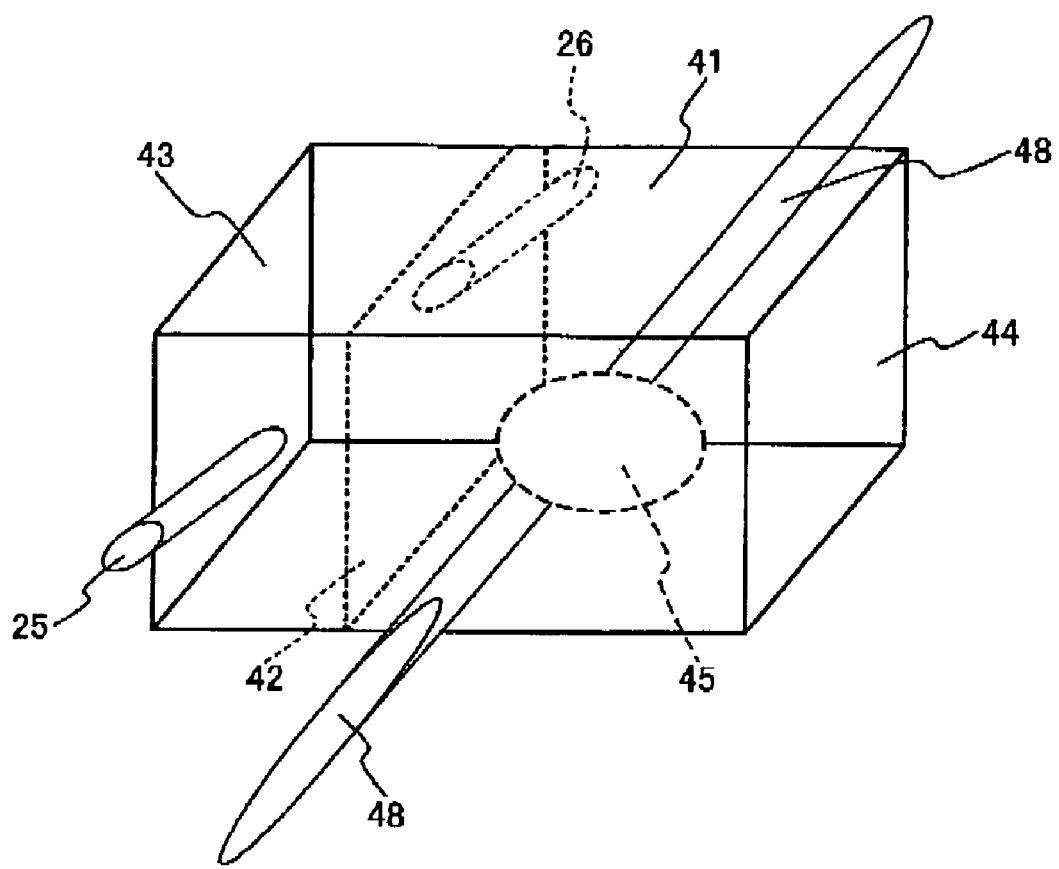
FIG. 8 is a diagram showing a modification of the cultivation vessel.

It is desirable that the artificial matrix pipe 48 is provided for the artificial matrix 45 as shown in FIG. 8, to cultivate a large-sized artificial organ. The one end of the artificial matrix pipe 48 is connected with the supply pipe 25 shown in FIG. 4, and the other end is connected with the discharge pipe 26. Thus, the culture fluid is passed inside the artificial matrix pipe 48. When the tissue to be formed on the artificial matrix 45 is large-sized, it is difficult to supply the material necessary for multiplication into the tissue. The artificial matrix pipe 48 in which the culture fluid is passed acts as an artificial vein and the material necessary for multiplication is supplied inside the tissue. When the artificial matrix pipe 48 is provided, the artificial matrix pipe 48 can support the artificial matrix 45. As shown in FIG. 8, the artificial matrix support sections 46 and 47 do not have to be always provided.

The third embodiment of the cell cultivation apparatus according to the present invention can be form the tissue with the 3-dimensional structure, like the first and second embodiments. Also, in the third embodiment, it is possible to cultivate a large-sized tissue.

(Fourth Embodiment)

The 3-dimensional klinostat according to the fourth embodiment of the present invention is used as a part of a plant growing apparatus. The plant growing apparatus in the fourth embodiment rotates a growth vessel accommodating a plant around the 2 axes and the gravity applied to the plant as the growth object is distributed into 3-dimensional directions. The plant growing apparatus in the fourth embodiment is used to confirm the physiological activity of the plant under the environment the gravity is distributed 3-dimensionally.

The plant growing apparatus in the fourth embodiment which rotates the growth vessels around the 2 axes has the same structure as the cell lump cultivation apparatus in the first embodiment approximately but is different from the first embodiment on the following points.

Figure 9:
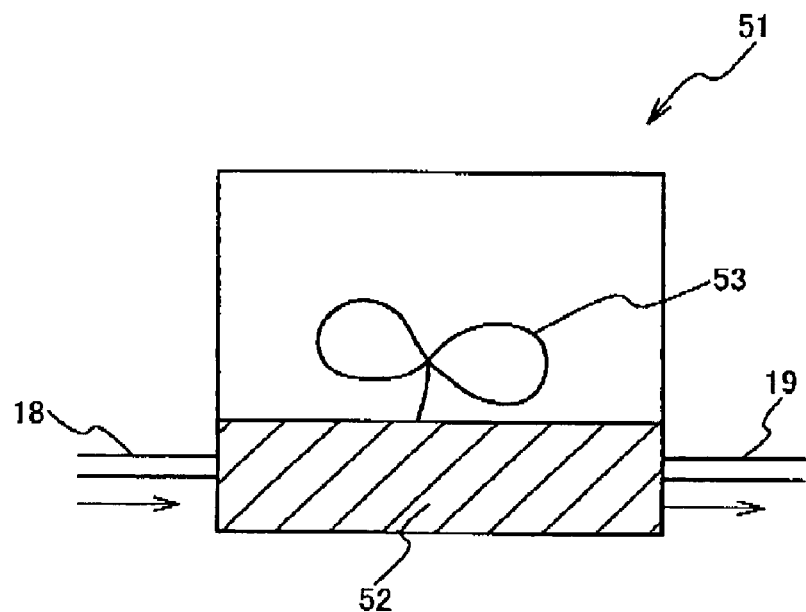
FIG. 9 is a diagram showing the structure of a growth vessel 51 used in the third embodiment of the present invention.

The growth vessel 51 shown in FIG. 9 is first used instead of the cultivation vessel 2 used in the first embodiment. The growth plant is accommodated in the growth vessel 51. The details of the growth vessel 51 are later mentioned.

Second, not the culture fluid but growth liquid is accumulated in the tank 3 shown in FIG. 4. The growth liquid is controlled to contain the material necessary to grow a plant. The growth liquid accumulated in the tank 3 is supplied to the growth vessel 41 through the rotary joint 8 and the rotary joint 12. The excessive growth liquid is discharged from the growth vessel 41 and is discharged to the tank 3 through the rotary joint 8 and the rotary joint 12. It is desirable that the tank 3 has the function to adjust the concentration of the material necessary to grow the plant the oxygen concentration and pH of growth liquid.

As shown in FIG. 9, the above-mentioned growth vessel 51 is connected with a supply pipe 18 and a discharge pipe 19. The growth liquid is supplied from the supply pipe 18 to the growth vessel 51 and the excessive growth liquid is discharged from the discharge pipe 19. The growth vessel 51 has a water keeping member 52 like lock wool therein. The growth liquid supplied to the growth vessel 51 is filtered into the water keeping member 52. The plant 53 as the growing object is planted in the water keeping member 52, and the plant 53 absorbs the material necessary to grow from the growth liquid filtered into the keeping member 52.

The plant growing apparatus in the fourth embodiment supplies the growth liquid to the growth vessel 51 in the state which the growth vessels 51 is rotated around the 2 axes, and discharges the growth liquid from the growth vessel 51, so that the growth liquid in the growth vessel 51 can be exchanged. The plant growing apparatus is not needed to stop the rotation of the growth vessel 51 to supply, discharge or exchange the growth liquid to the growth vessel 51 and is suitable to grow a plant under the rotation environment for a long term.

It should be noted that in the fourth embodiment, the growth vessel 51 is rotated around the 2 axes. However, the growth vessel 51 may be rotated around two or more axes.

Also, the plant growing apparatus in the fourth embodiment can be applied to the growth of a microorganism like mold. In this case, the microorganism is stored in the growth vessel 51 instead of plant 53 and is grown.

(Fifth Embodiment)

The 3-dimensional klinostat according to the fifth embodiment of the present invention is used as a part of an aquatic organism growing apparatus. The aquatic organism growing apparatus in the fifth embodiment rotates the growth vessel accommodating the aquatic organism as the growth object around the 2 axes. The gravity applied to the aquatic organism as the growth object is distributes in all the directions 3-dimensionally. The aquatic organism growing apparatus in the fifth embodiment is used to confirm the activated course of the physiological activity of the aquatic organism under the environment in which the gravity is distributes in all the directions 3-dimensionally.

The aquatic organism growing apparatus in the fifth embodiment has substantially the same structure as the cell lump cultivation apparatus in the first embodiment and differs from the first embodiment in the following points.

Figure 10:
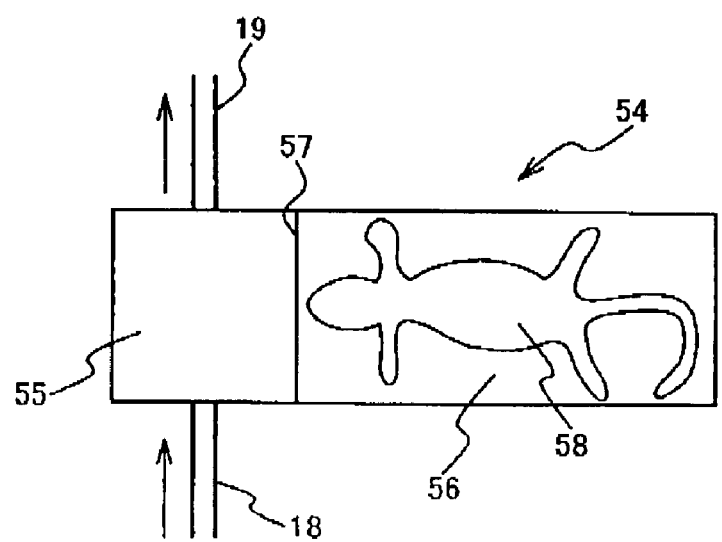
FIG. 10 is a diagram showing the structure of a growth vessel 54 used in the fourth embodiment of the present invention.

First, the growth vessel 54 shown in FIG. 10 is used instead of the cultivation vessel 2 in the first embodiment. The aquatic organism is accommodated in the growth vessel 54. It is desirable that the aquatic organism to be grown may be any of an animal, a plant and a microorganism, e.g., a newt, a fish, a aquatic plant. The details of the growth vessel 54 are mentioned later.

Second, breeding water is accumulated in the tank 3 shown in FIG. 4 instead of the culture fluid. The breeding water is controlled to contain the material necessary to grow the aquatic organism. When the aquatic organism is an animal, the bait of the aquatic organism is mixed with the breeding water and is supplied to the growth vessel 54. The breeding water is accommodated in the tank 3 and is supplied to the growth vessel 54 through the rotary joint 8 and the rotary joint 12. The excessive breeding water is discharged from the growth vessel 54 and is discharged to the tank 3 through the rotary joint 8 and the rotary joint 12. It is desirable that the tank 3 has a gas exchange function to adjust the gas concentration of the breeding water, a control function of pH, and a removal function to remove egesta from the aquatic organism.

As shown in FIG. 10, the above-mentioned growth vessel 54 contains a flow path room 55 and a growth room 56. The supply pipe 18 which supplies the breeding water and the discharge pipe 19 which discharges the breeding water are connected with the flow path room 55. The flow path room 55 is separated from the growth room 56 by a separation member 57. A lot of holes are provided for the separation member 57. Through the holes, the exchange of the culture fluid between the flow path room 55 and the growth room 56 is carried out. The aquatic organism 58 is put in the growth room 56 and the cultivation for the growth of the aquatic organism 58 is carried out in the growth room 56.

Figure 11:
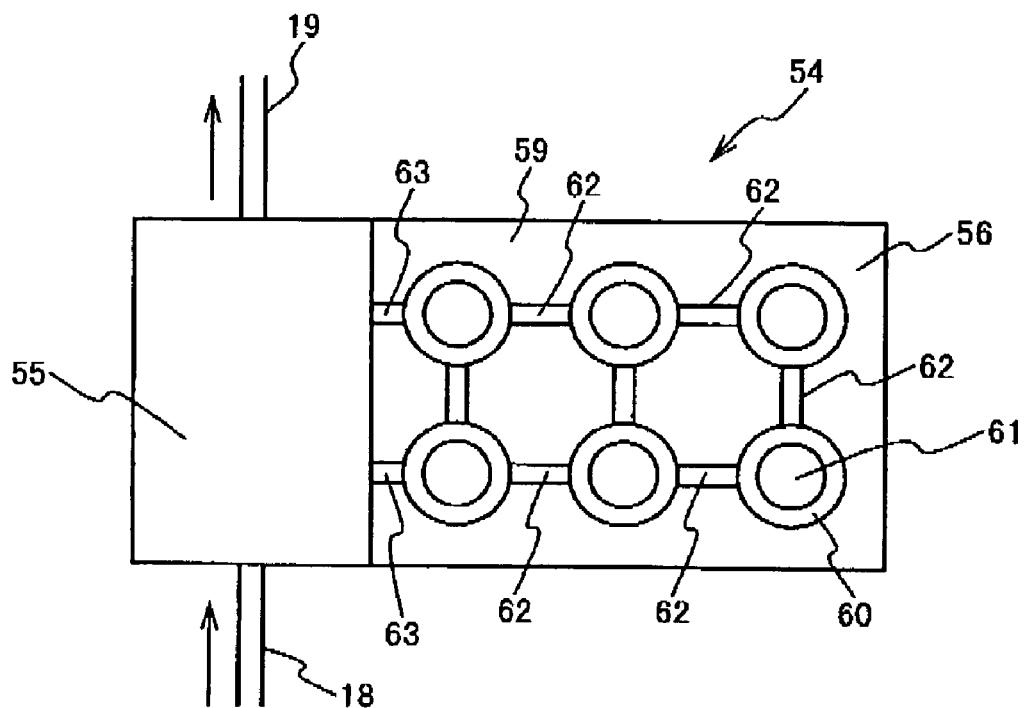
FIG. 11 is a diagram showing the structure of a modification of a growth vessel.

When eggs of the aquatic organism 58 are grown, an egg holder 59 is preferably stored in the growth room 56, as shown in FIG. 11. A plurality of egg storage rooms 60 which are cylindrical holes are provided for the egg holder 59, and the eggs 61 are stored in the egg storage rooms 60 and are fixed therein. Neighbor egg storage rooms 60 are connected with each other by flow paths 62, and the flow path 63 is provided for ones of the egg storage room 60 which face to the flow path room 55 and connected with the flow path room 55. The breeding water is supplied to each egg storage room 60 through the flow path 62 and the flow path 63.

The aquatic organism growing apparatus in the fifth embodiment supplies the breeding water to the growth vessel 54 and discharges from the growth vessel 54, in the rotation state of the growth vessels 54 around of the 2 axes, so that the breeding water in the growth vessel 54 can be exchanged. The aquatic organism growing apparatus needs not to stop the rotation of the growth vessel 54 to supply the breeding water to the growth vessel 54. Therefore, it is suitable to grow the aquatic organism for a long term under the rotation environment.

It should be noted that in the fifth embodiment, the growth vessels 54 are rotated around the 2 axes. However, the growth vessel 54 can be rotated around 2 or more axes.

(Sixth Embodiment)

The 3-dimensional klinostat according to the sixth embodiment of the present invention is used as a part of the animal growing apparatus. The animal growing apparatus in the sixth embodiment rotates the growth vessel, which accommodates an animal as an growth object, around the 2 axes to distribute the direction of the gravity applied to the animal as the growth object 3-dimensionally. The animal growing apparatus in the sixth embodiment is used to confirm the activated course of the physiological activity of the animal under the environment in which the direction the gravity is distributed 3-dimensionally.

The animal growing apparatus in the sixth embodiment has substantially the same structure as the cell lump cultivation apparatus in the first embodiment but differs from the first embodiment in the following points.

Figure 12:
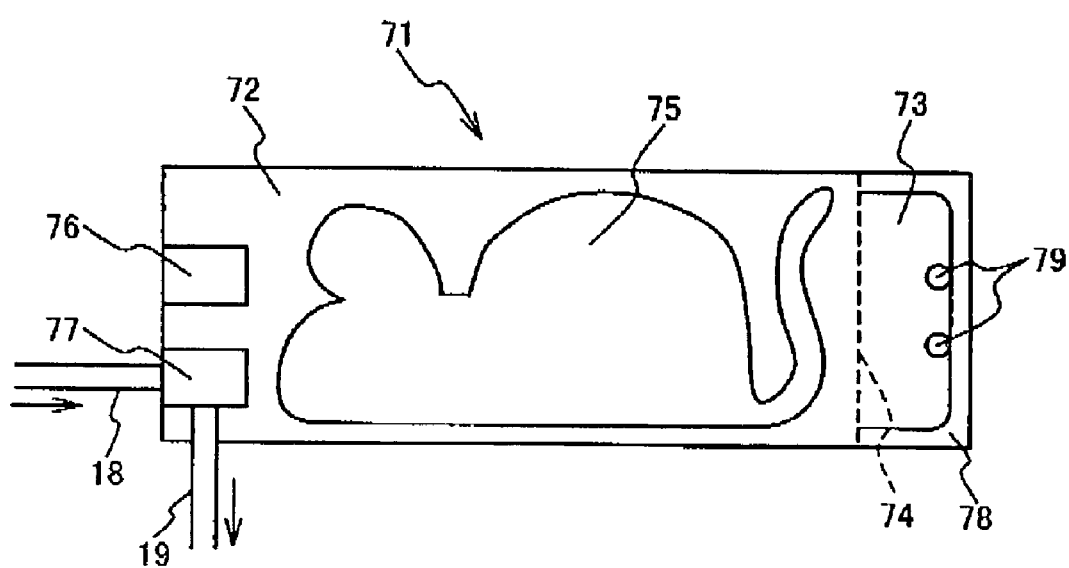
FIG. 12 is a diagram showing the structure of a growth vessel 71 used in the fifth embodiment of the present invention.

First, the growth vessel 71 shown in FIG. 12 is used instead of the cultivation vessel 2 used in the first embodiment. An animal to be grown, e.g., a mouse is housed in the growth vessel 71. The details of the growth vessel 71 are later mentioned.

Second, it is not the culture fluid but drinking water that is accumulated in the tank 3 shown in FIG. 4. The drinking water accumulated in the tank 3 is supplied to the growth vessel 71 through the rotary joint 8 and the rotary joint 12.

Third, a discharge pipe 21 is not connected with the tank 3. The old drinking water after being supplied to the growth vessel 71 is discharged to the discharge pipe 21 through the rotary joint 12 and the rotary joint 8. The drinking water is discharged to the discharge pipe 21 and is dumped away just as it is.

As shown in FIG. 12, a growth room 72 and an excrement processing room 73 are provided for the above-mentioned growth vessel 71. The growth room 72 accommodates the animal 75 as a growth object. It is desirable that the growth room 72 has such a size as the animal 75 cannot change the direction of itself. A bait box 76 and a drinking water supply vessel 77 are provided for the growth room 72. The bait box 76 supplies the bait to the animal 75. The drinking water supply vessel 77 is connected with the supply pipe 18. As described above, the supply pipe 18 is connected with the tank 3 through the rotary joint 8 and the rotary joint 12. The supply pipe 18 supplies the drinking water accumulated in the tank 3 to the drinking water supply vessel 77. The drinking water supply vessel 77 supplies the drinking water supplied from the supply pipe 18 to the animal 75. Also, the drinking water supply vessel 77 is connected with the discharge pipe 19. The old drinking water after being supplied to the drinking water supply vessel 77 is discharged from the discharge pipe 19 through the rotary joint 12 and the rotary joint 8 to the discharge pipe 21. The drinking water is discharged to the discharge pipe 21 and is thrown or dumped away just as it is. The growth room 72 is separated from the excrement processing room 73 by a network 74.

An adhesive sheet 78 and a moisture absorbing member 79 are provided for the excrement processing room 73. The adhesive sheet 78 captures the shit discharged from the animal 75. The moisture absorbing member 79 absorbs urine discharged from the animal 75. The sanitary state of the growth room 72 is maintained by the adhesive sheet 78 and the moisture absorbing member 79.

The animal growing apparatus described above in the sixth embodiment supplies drinking water to the growth vessel 71 in the rotation state of the growth vessels 71 around the 2 axes, and discharges the drinking water from the growth vessel 71, so that the drinking water supplied to the growth vessel 71 can be exchanged. The animal growing apparatus needs not to stop the rotation of the growth vessel 71 to supply drinking water to the growth vessel 71 and to discharge or to exchange. It is suitable to grow the animal for a long term under the rotation environment.

It should be noted that in the sixth embodiment, the growth vessels 71 are rotated around the 2 axes but the growth vessel 71 can be rotated around two or more axes.

The practical technique to cultivate the tissue with the 3-dimensional structure through the cultivation of the cell is provided according to the present invention.

Also, according to the present invention, a technique that the separation of the cell lump can be prevented is provided when the tissue with the 3-dimensional structure is formed.

Also, according to the present invention, a technique that can cultivate the cell for a long term is provided when the tissue with the 3-dimensional structure is formed.

Also, according to the present invention, a technique that the environment of the cultivation of the cell can be optimized is provided when the tissue with the 3-dimensional structure is formed.

Also, according to the present invention, a technique which can cultivate a large-sized tissue with a 3-dimensional structure is provided.

What is claimed is:

1. A method of growing and cultivating cells, comprising:
a) encapsulating the cells and a fluid in a vessel, wherein said vessel is part of a rotating unit;
b) rotating said vessel around different n axes, wherein n is an integer greater than 1; and
c) continuously flowing fluid through a flow path formed between the vessel and an external fluid tank, while said vessel is rotating.

2. The method according to claim 1, further comprising adjusting a coefficient of viscosity of said fluid such that said cells do not touch and attach to said vessel.

3. The method of claim 1, wherein said c) continuously flowing fluid comprises:
pumping fluid into said vessel;
circulating said fluid within said vessel; and
withdrawing fluid from said vessel.

4. A method of growing and cultivating cells, comprising:
a) encapsulating the cells and a fluid in a vessel, wherein said vessel is part of a rotating unit,
said rotating unit comprising an inner frame, an outer frame and a base, said inner frame connected to said outer frame via a first rotary joint, and said outer frame connected to said base via a second rotary joint, wherein said vessel is connected to said inner frame;
b) rotating said vessel around different n axes, wherein n is an integer greater than 1,
wherein said rotating comprises rotating the inner frame about a first one of the different n axes via said first rotary joint, and rotating the outer frame about a second one of the different n axes via said second rotary joint; and
c) continuously flowing the fluid through a flow path defined between the vessel and an external fluid tank, while said vessel is rotating,
wherein said flow path goes through the first and second rotary joints within the rotating unit.

* * * * *